United States Patent [19]

Honrud

[11] Patent Number: 5,031,237
[45] Date of Patent: Jul. 16, 1991

[54] LIGHT ACTUATED AIR RECIRCULATING AND FILTRATION SYSTEM

[76] Inventor: Gregory S. Honrud, 500 S. State St., Bellingham, Wash. 98225

[21] Appl. No.: 446,084

[22] Filed: Dec. 5, 1989

[51] Int. Cl.$^5$ ................................................ A61F 9/06
[52] U.S. Cl. ........................................ 2/8; 2/171.3; 128/201.25
[58] Field of Search .................. 2/8, 171.3, 5, 7, 9, 2/424, 436, 437; 128/201.25, 201.23, 201.24, 201.22, 206.12, 206.21

[56] References Cited

U.S. PATENT DOCUMENTS

| | | | |
|---|---|---|---|
| 911,476 | 2/1909 | Cheesman | 2/8 X |
| 2,103,006 | 12/1937 | Helfenstein et al. | 2/8 |
| 3,238,535 | 3/1966 | Richey | 2/8 |
| 3,629,868 | 12/1971 | Greenlee | 2/8 |
| 3,921,223 | 11/1975 | Hoyecki | 2/8 |
| 3,943,573 | 3/1976 | Budmiger | 2/8 |
| 4,071,912 | 2/1978 | Budmiger | 2/8 |
| 4,309,774 | 1/1982 | Guzowski | 2/8 |
| 4,498,202 | 2/1985 | Yamamoto | 2/171.3 X |
| 4,852,562 | 8/1989 | Howie | 2/171.3 X |

FOREIGN PATENT DOCUMENTS 0193031 4/1967 U.S.S.R. .................... 2/8

OTHER PUBLICATIONS

Brochure titled, "RACAL Introduces POWERFLOW Air You Can Wear Almost Anywhere!", Feb. 1986.
Brochure titled, "3M Occupational Health & Safety Products".

Primary Examiner—Peter Nerbun
Attorney, Agent, or Firm—Cassidy, Vance & Tarleton

[57] ABSTRACT

The present invention comprises apparatus and methods of using a light sensitive switch, such as a photoelectric or photo-resistive cell, to actuate a battery powered electric motor which rotates a fan blade located within a housing near a facial area of a welding helmet. When exposed to a high intensity light, such as the light emitted during a welding process, the photoconductive cell actuates the battery powered motor. When activated, the motor rotates the fan blade which draws air away from the face of a wearer and passes such air through a filter into an air flow chamber, thereby, filtering the drawn air. The rotation of the fan blade then forces the filtered air toward the facial area of the wearer. A smoke block, which restricts the entrance of smoke or other contaminated vapors from entering the confines between the interior surface of the helmet and the face of the wearer, may be removably attached to the helmet.

8 Claims, 6 Drawing Sheets

LIGHT ACTUATED AIR RECIRCULATING AND FILTRATION SYSTEM

TECHNICAL FIELD

The present invention relates to a light actuated, air recirculating and filtration system, and, more particularly, to apparatus and methods of using a light sensitive switch, such as a photoconductive cell, to activate a battery powered motor which rotates an air filtration and/or ventilation fan located near a facial area of a welding helmet or hood.

BACKGROUND ART

Within the welding industry there has been a long standing need to protect the vision and respiration of welders. Budmiger (U.S. Pat. No. 4,071,912; issued Feb. 7, 1978) is an example of a welder's mask which was specially designed to protect a welder's vision.

Although many welding helmets protect the welder's eyes from the intense light generated by the welding arc, the vapors and heat captured and generated between the welder and the helmet is a significant disadvantage. Consequently, various helmets were created that incorporated the use of internal ventilation and filter systems. The following disclosures relate to such helmets: Richey (U.S. Pat. No. 3,238,535; issued Mar. 8, 1966); Greenlee (U.S. Pat. No. 3,629,868; issued Dec. 28, 1971); Hoyecki (U.S. Pat. No. 3,921,223; issued Nov. 25, 1975); Budmiger (U.S. Pat. No. 3,943,573; issued Mar. 16, 1976); and Guzowski (U.S. Pat. No. 4,309,774; issued Jan. 12, 1982).

More particularly, Richey ('535) discloses a welding helmet having solar cells mounted thereon. The solar cells produce electrical power when energized by the incident light from an arc welding process. The electrical power is conveyed to a motor which rotates fan blades. The fan blades draw air toward the center of a tube. The air then passes through a longitudinal apertured slot and is directed downwardly along the interior of the front surface above the hood. The inlet ports of the tube are provided with cylindrical filter elements.

Greenlee ('868) discloses a complex adapter assembly for a welding helmet, wherein an electric motor and fan are detachably secured to the forward portion of a protective helmet so as, when actuated, to draw air into the mask or helmet generally about the operator's head and expelling such air through a forwardly directed opening formed in the mask. A mercury-type switch assembly, which performs according to the attitude of the helmet, is used to actuate the device. The fourth embodiment discloses the use of batteries which are immediately adjacent to the fan.

Hoyecki ('223) discloses an air shield comprising a hollow tube perforated along its length and contoured to encircle the neck of a welder. An exterior air supply is provided and attached to the device by means of a tube and on-off valve.

Budmiger ('573) discloses a protective helmet having a mini-fan and a cold air channel for supplying cooling air to the electronic and electromagnetic devices of a shading means and to an eye shade.

Guzowski ('774) discloses a ventilating helmet having an electrically operated fan which is adapted to move air to the interior of the helmet. The electrically operated fan is operated by a solar cell which is directly exposed to a source of light energy.

The teachings and devices disclosed in the foregoing patents have inherent difficulties. For example, solar cells often do not produce sufficient electrical power to properly rotate a fan. Solar cells also become easily broken and become covered with thick welding smoke. Each of these devices draws air either from a separate air supply line or from exterior areas of the hood. The maneuverability of the welder is severely restricted if use of a separate air hose is required. In other words, the welder must contend with a trailing air tube each time he or she wants to move. Air hose lines are cumbersome, expensive, and inconvenient. As a welder performs various tasks, there are times when he needs ventilation and times he does not. However, it is inconvenient for a welder to be switching the ventilator on and off during a period of work. An air supply obtained through an air hose is controlled manually with an on-off valve.

During a welding process, smoke and heavily contaminated air generally surround the welder. If air is drawn from the exterior areas of the hood, as taught in the prior art, then such contaminated air is drawn or blown past the facial area of the welder.

Many of the devices disclosed in the prior art are also very complex, expensive, and difficult to manufacture. Other difficulties include, the fact that if the bulk of the weight of such a device is located near the lower-most areas of the hood, it is difficult to maintain the hood in a raised position. If a mercury-type switch assembly is used and the hood is located in a lowered position, the switch assembly would actuate the motor, whether or not an arc had been struck.

Various brochures, such as those titled "RACAL Introduces POWERFLOW Air You Can Wear almost Anywhere!" and "3M Occupational Health & Safety Products", disclose other types of protective head and respiratory gear which do not pertain to the welding industry.

The inventor believes the known prior art taken alone or in combination neither anticipate nor render obvious the present invention. These citations do not constitute an admission that such disclosures are relevant or material to the present claims. Rather, these citations relate only to the general field of the disclosure and are cited as constituting the closest art of which the inventor is aware.

DISCLOSURE OF INVENTION

It is the general object of the present invention to provide apparatus and methods for protecting the vision and respiration of a welder by providing a welding helmet or hoodlight with a light actuated, air recirculating and filtration system capable of: breaking up any heavily laden smoke or contaminated vapors which may pass between the helmet and the welder; drawing such air and vapors through a filter; and expelling the filtered air toward the face of the welder.

A further object of the present invention is to provide an apparatus which may be wholly incorporated into the design and housing of the helmet, thereby, eliminating the need for an external, remote battery pack or electrical supply, and associated electrical cable.

Another object is to provide an apparatus which conserves electrical energy by only operating when a light sensitive switch is exposed to a high intensity light, as occurs during a welding process, thereby, reducing the need to stop work to change or recharge the batteries.

Another object is to provide an apparatus having a removable, smoke block to restrict the entrance of smoke or other contaminated vapors into the confines between the helmet and the face of the welder.

The present invention achieves these general and specific objects and presents new apparatus and methods for protecting the vision and respiration of a welder which incorporates therein the beneficial features of the prior art. The present invention also overcomes each of the previously mentioned disadvantages.

The act of welding, either with a torch or electric arc method, produces most of the adverse fumes that a welder is subjected to. The ambient fumes are not as much of a factor. When a welder, dons his helmet and starts welding, smoke is produced and ventilation is needed.

The concept of the present invention is that an intense-light sensing means, such as a photo-electric cell, may be connected to a power source and to an electric motor to drive means of ventilating the space between a welding helmet or hood and the wearer. A filtration system may also be used to filter the drawn air and then project the filtered air into the facial area of the wearer.

To achieve these ends, the present invention comprises apparatus and methods of using a light sensitive switch, such as a photo-electric or photo-resistive cell, to activate a battery powered motor which rotates an air circulation and/or filtration fan located near a facial area of a welding helmet. In response to the high intensity light emitted during a welding process, the light sensitive switch or photoconductive cell selectively actuates the battery powered ventilating motor. When activated, the motor rotates a fan which in turn circulates air within the confines between the interior surface of a welding helmet and the face of a wearer. Circulation occurs by the fan drawing air from within said confine into an air flow chamber and then forcing the circulated air towards the facial area of the wearer.

Typically, the helmets from the prior art provide an external power pack or power source to drive a ventilation fan, and require the welder to either manually activate and inactivate the ventilation system or simply leave the power on during the whole work day. The required batteries, however, are expensive and bulky, and create an inconvenience of their own.

In contrast, the present system only ventilates the helmet when the person is actually welding. This is more convenient than the conventional helmet, and greatly reduces the amount of energy consumed by the fan as compared to having the fan continually operate. Solar cells are not used to power the device. Rather, the light sensitive switch or photoconductive cell is used as a trigger mechanism to close and open a circuit between at least one battery and an electric motor having a fan blade secured thereto.

This invention uses a battery pack for a power source, rather than depending upon an ineffective method of using solar cells to power the fan. Thus, the power or electricity for the fan is not produced by from the arc itself. In the preferred embodiment, the inventor uses Ni-cad batteries. Ni-cad batteries are non-explosive and are relatively compact in size. Such batteries may be easily attached to the hood, either within the interior cavity defined by the hood or to an exterior portion of the hood. The Ni-cad batteries are rechargeable having a charge which lasts between 6 to 10 hours depending upon the amount and length of welding performed. After a day's use or after the charge has been depleted, the batteries may be plugged into a power source and be recharged.

The hood may be provided with a battery housing which allows for easy attachment and removal of the battery pack and connection to the proper lead wires.

Once the battery pack is recharged it may be easily replaced within its battery housing for operation of the fan. The battery pack may be provided with a pair of female terminal leads which allow for easy attachment and removal. One of the leads passes to the photoconductive cell. The other lead passes to the fan motor. Another electrical path is provided between the photoconductive cell and the fan motor.

The battery pack may also be provided with appropriate contacts so that the batteries may be plugged into a recharging source without requiring their removal from the hood.

Once the fan is activated, an air flow is urged against the face of the user. The fan serves to recirculate the air between the welding helmet and the face of the user, and to partially pressurize that space. Thus, the hood becomes semi-pressurized a moment after the arc is struck. As the smoke rises from the welding processes, the air flow which is forced against and around the face of the user propels such smoke away from the user. The fan creates a positive pressure behind the hood, which in turn, eliminates respiratory fatigue commonly associated with negative pressure respirators, thus, increasing efficiency and output. The positive pressure also gives comfort by not only keeping dust and smoke out, but also keeps the lens or viewing window fog-free This design cools the user and filters the air which is available to the user to breathe. This increases comfort and protection of the user. Air blowing into the face of the welder also keeps the welder alert reducing the possibility of costly errors or injuries.

Although a primary purpose of the present invention is to cool the operator during use and break up and dispel noxious fumes, an additional benefit is that the invention may serve as a filtration system to filtrate noxious fumes. Filtration occurs when a filter is place upon or near the air intake vents of the apparatus. When the fan is activated, the fan draws air from within said confined area through a filter and into an air flow or filtration chamber, thereby, filtering the drawn air, and forcing the filtered air toward the facial area of the wearer.

On occasion, the welder may need to weld a continuous bead that requires a welding run of approximately 25 to 30 seconds. Such a welding run is unusually long, and will probably not be exceeded because an even longer run would require the welder to reposition himself or herself to obtain an adequate contact with the surface being welded. If such a long run is encountered, some contaminated smoke may be drawn into the hood. However, such smoke is first drawn through one or more filters which clean the air before the air is blown into the face of the user.

Even before the contaminated smoke reaches the filtration means, it is dispersed by the eddies and air currents created by the rotation of the fan blade. For example, the motor and fan blade of the present invention blows 14 to 16 cubic feet per minute, which is a large volume of air to run inside such a small area. Instead of the smoke rolling up into the face of the operator in a more solid form, such smoke, which forms the foul or contaminated air, becomes dissipated before it passes into the filters. This is the primary reason why the filtration system is located so closely to the outlet system of the fan. The air currents actually break up the molecules of the smoke laden air before entering the filtration system. After passing through the filters, the cleansed air is blown into the face of the operator and then recycled back into the filtration system.

To further eliminate having noxious fumes from entering the apparatus, a smoke block pad is provided to restrict the entrance of smoke or other contaminated vapors from entering the confines between the interior surface of the helmet and the face of the wearer. The smoke block dramatically increases the efficiency of the filtration system. Basically, the smoke block is removably attached to the lower end of the hood in such a manner that when the hood is lowered, during the welding process, the smoke block seals or partially seals the space between the user's throat and the hood. The smoke block prevents smoke from entering up into the hood from below the user's throat and chin. Since the space between the hood and the user's face is partially pressurized, a plenum is created which urges the smoke away from the helmet. The smoke block conforms to the chin and/or neck of the wearer and to the lower wall of the helmet, and is removable, durable, and easily washed.

Without the smoke block, heavy, thick smoke could be easily drawn up into the hood and into the filtration system. The thickness and porosity of the filter material may be varied to accommodate various applications of this invention. For example, a High Efficiency (HEPA) filter may be used for dust (including asbestos), fumes, mists, radionuclides, and radon daughters.

This invention is extremely simple and compact in design and operation, and eliminates the need for a breathing tube assembly or supply air line, thus, giving the welder complete mobility, without any trailing air lines. No compressed air hoses are required. The user may move freely without worrying of tangled compressed air hoses or battery cables.

The design of the present invention does not require the hood to be secured against the face of the user. This feature is significantly different from the full face-piece shown in the Racal POWERFLOW brochure. Instead, a hood comprising the present invention is worn in a traditional manner. A conventional hood head gear is used to secure the hood to the wearer. Thus, multiple users may safely use the hood without requiring a dirty, possibly abrasive or corrosive mask be secured to the wearer's face. The fan and filtration system are placed within a housing placed within the hood. A rectangular opening is provided within the hood to accommodate the placement of such housing.

This invention may be marketed in a kit format. The kit would enable an operator to easily modify a commercially available welding hood to incorporate this invention. Since there are a wide variety of existing helmets, each with a different following of patronage, the kit format allows an operator to modify his or her own preferred welding helmet to comprise the invention. Alternatively, a welding hood having the invention incorporated therein may also be manufactured and marketed.

These and other objects and advantages of the present invention will become more readily apparent upon reading the following disclosure and referring to the attached drawings.

One should understand the drawings are not necessarily to scale and the elements are sometimes illustrated by graphic symbols, phantom lines, diagrammatic representations, and fragmentary views. In certain instances, the inventor may have omitted details which are not necessary for an understanding of the present invention or which render other details difficult to perceive.

BEST MODE FOR CARRYING OUT THE INVENTION

Figure 3:
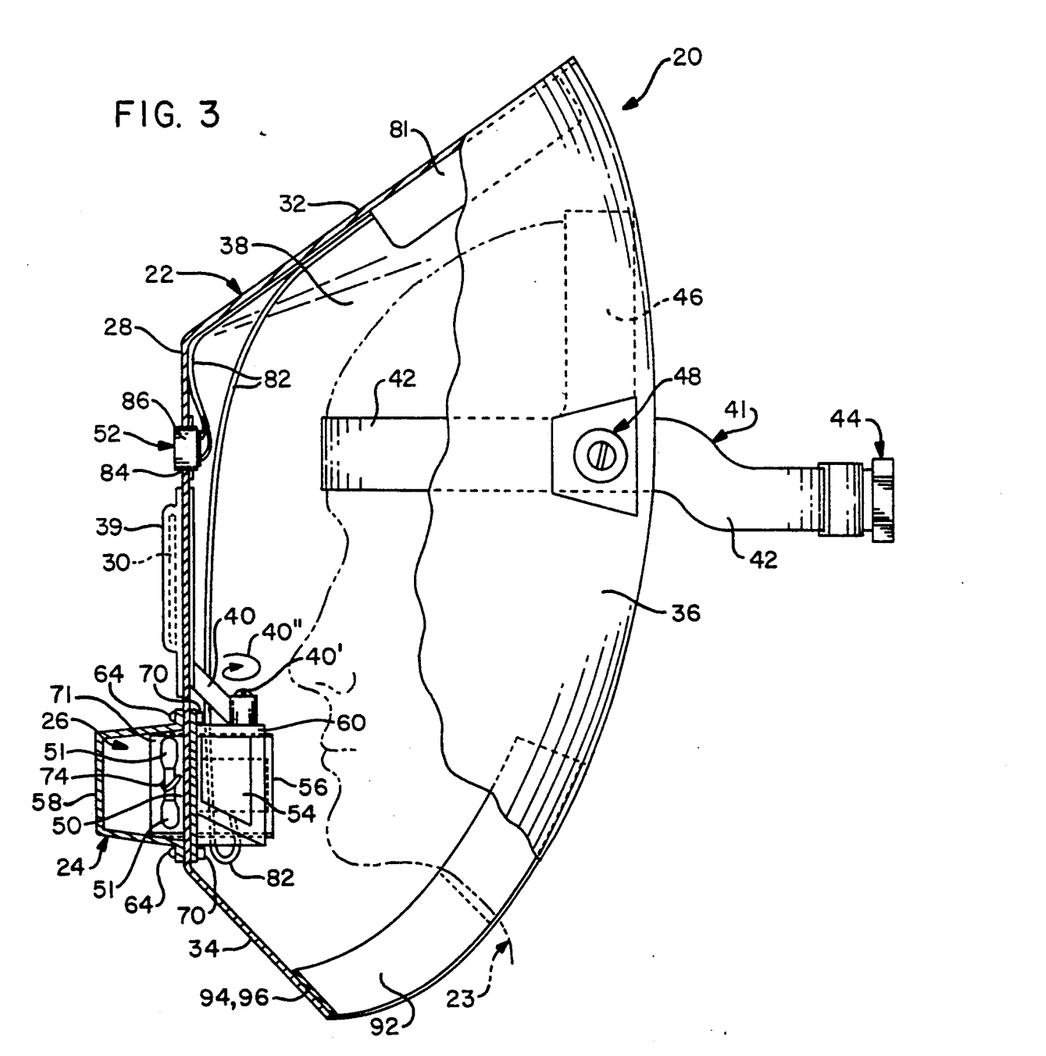
FIG. 3 is a fragmentary, cross-sectional, side-elevational view of the apparatus.

Referring to the drawings and particularly to FIG. 3, wherein like numerals indicate like parts, light actuated, air recirculating and filtration system 20 generally comprises a welding helmet 22 having means of, when exposed to an intense light, automatically breaking up smoke and/or contaminated vapors which may pass between helmet 22 and a person 23 wearing helmet 22, drawing such air and vapors into a housing 24 defining an air flow chamber 26, and expelling the filtered air from air flow chamber 26 toward the facial area of person 23.

Welding helmet 22 may have any appropriate configuration which protects the facial area and vision of person 23. There are many conventional welding helmets 22 which are currently being used within the welding industry that may be modified to incorporate therein the features of this invention. Alternatively, a unitary welding helmet 22 having the features of this invention may also be manufactured. Preferably, helmet 22 has: a protective front wall 28; a lens 30 located within front wall 28 through which person 23 may view work being performed; and rearwardly extending upper wall 32, lower wall 34, left wall 36, and right wall 38 which are formed integrally with front wall 28.

Lens 30 may be secured to helmet 22 by means of a frame 39 which is placed about an appropriately sized opening in front wall 28. In some welding applications it is desirable to replace lens 30 with a darker or lighter lens. At times, it may also be necessary to replace a broken lens 30. Helmet 22 is, therefore, provided with means for removing and replacing lens 30. Such means comprises an upper catch (not shown), a spring (not shown), and a lower locking mechanism 40. The upper catch retains the upper portion of lens 30 within frame 39. The spring is juxtaposed between frame 39 and lens 30. Lower locking mechanism 40 may comprise any adequate means for urging lens 30 against the spring within frame 39. When so urged, the spring serves to prevent vibration or movement of lens 30 and to cushion any outward impact that lens 30 may experience. In the preferred embodiment, lower locking mechanism 40 comprises a brace member which is pivotally secured to housing 24 by means of a bolt, screw 40', or rivet. When rotated as shown by arrow 40'', lower locking mechanism assumes a position that enables lens 30 to be removed from frame 39.

Helmet 22 may be attached to and worn by person 23 by using any conventional head gear 41. For example head gear 41 may comprise a generally horizontal head band 42 which may be tightened or loosened by means of an adjustment 44. Head gear 41 may also be provided with an over-head strap 46 which is attached to head band 42. Head gear 41 may be secured to helmet 22 by means of a ratchet mechanism 48 which permits helmet 22 to rotate between a lowered position in front of face of person 23 and a raised position above the head of person 23. FIGS. 1, 2, 3, 7 and 8 illustrate helmet 22 rotated to a lowered position.

The means for automatically breaking up smoke and/or contaminated vapors which pass between helmet 22 and person 23, drawing such air and vapors into air flow chamber 26 of housing 24, and expelling the filtered air toward the facial area of person 23, generally comprises: housing 24; an electric motor 50 having a fan blade 51 attached thereto; a light sensitive switch 52; and means for supplying electrical power to motor 50.

Figure 4:
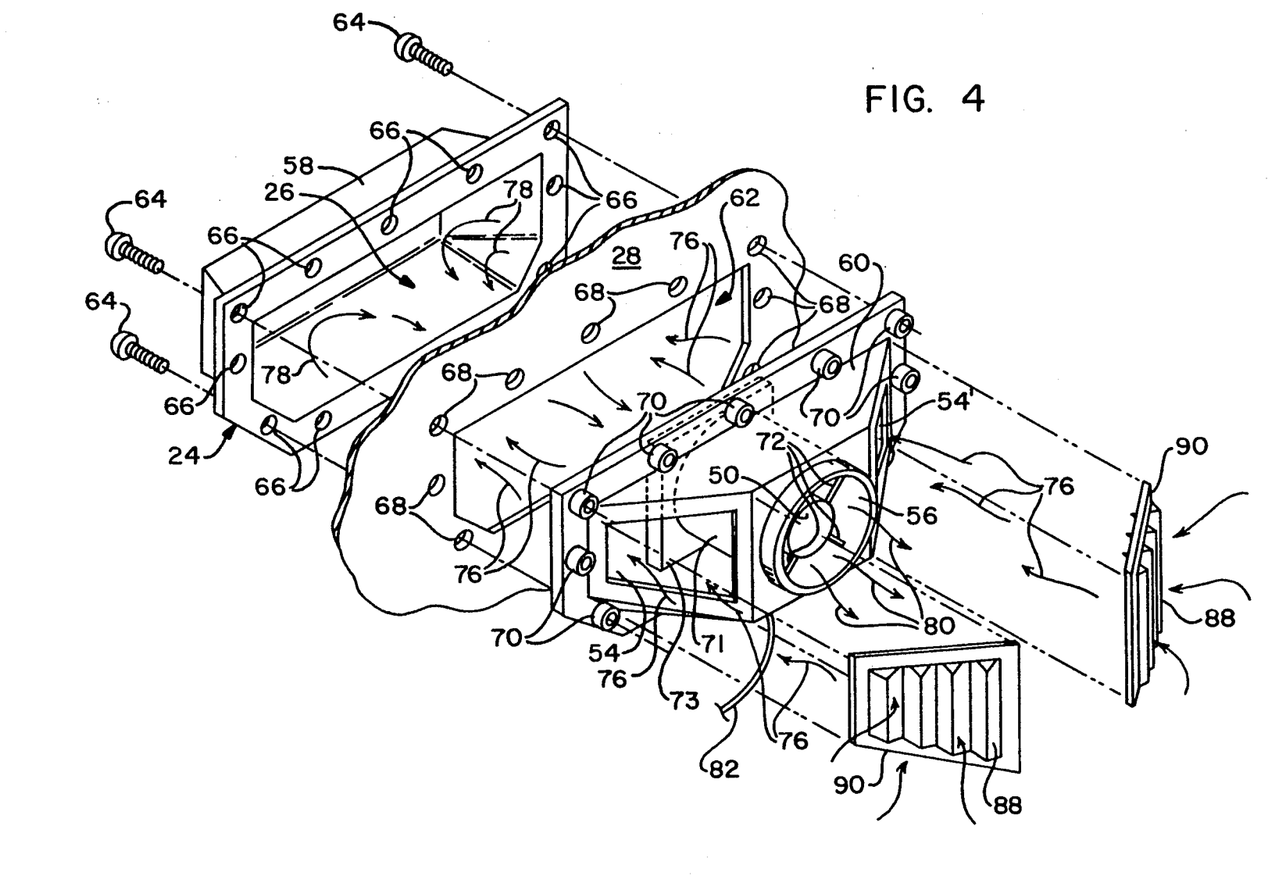
FIG. 4 is an exploded, schematic, isometric view of the housing, air flow chamber, motor, and filters of the present invention.

Housing 24 is either attached to or integrally formed within helmet 22, and defines air flow chamber 26. Referring now to FIG. 4, housing 24 and air flow chamber 26 have at least one air intake vent 54 or opening and at least one air exhaust vent 56 or opening. As shown in FIGS. 2, 4, 7 and 8, two air intake vents 54 and 54' are provided in the preferred embodiment.

Housing 24 is preferably located near the mouth and facial areas of person 23. For example, if a conventional welding helmet 22 is modified to incorporate therein the features of the present invention, housing 24 may comprise: an exterior cover 58; and an interior element 60. An appropriately sized opening or aperture 62 is provided in front wall 28. Exterior cover 58 and interior element 60 are juxtaposed against and attached to opposite sides of front wall 28 adjacent to aperture 62 in such a manner that air may pass through air intake vents 54 and aperture 62 into a cavity formed by exterior cover 58. Exterior cover 58 and interior element 60 may be attached to front wall 28 by any adequate means. In the preferred embodiment, bolts 64 are passed through bores 66 and 68 provided in exterior cover 58 and front wall 28, respectively. Bolts 64 are then attached to nuts 70 formed within interior element 60. In an alternative embodiment, helmet 22 is molded to incorporate either exterior element 60 or interior element 60 within the design of front wall 28. The combination of exterior cover 58 and interior element 60 forms housing 24 and defines the outer boundaries of air flow chamber 26.

In the preferred embodiment, electric motor 50 is positioned within air flow chamber 26 and is appropriately mounted to interior element 60. The mounting means for motor 50 may comprise a conduit 71, having inwardly extending brace members 72 which is secured to interior element 60 within air flow chamber 26. Motor 50 is attached to brace member 72 within conduit 71. Conduit 71 may also have an exterior brace 73 which is located near exterior cover 58. Conduit 71 serves the function that once air enters air flow chamber 26, such air must pass along a substantial length of chamber 26 before being redirected by fan blade 51. Fan blade 51 redirects and urges such air into conduit 71, whereafter such air is expelled from air flow chamber 26 through exhaust vent 56. The depth of exterior cover 58 must be sufficient to accommodate placement of motor 50 and conduit 71 therein, and still enable the drawn air to circulate within air flow chamber 26.

The inventor believes that the location of fan blade 51 should be on the other side of motor 50, away from the facial area of person 23. Thus, housing 24 would receive the impact and retain any debris if a fan blade 51 were to break or become damaged, and injury to person 23 could be avoided.

Motor 50 has a driven, rotatable shaft 74, shown in FIG. 3, protruding therefrom. At least one fan blade 51 is located within air flow chamber 26 and is secured to shaft 74 in such a manner that when shaft 74 is rotated, fan blade 51 draws air into air flow chamber 26 through air intake vents 54 and expels such air outward through conduit 71 and air exhaust vent 56.

In essence, when activated, motor 50 rotates fan blade 51 to create a vacuum plenum within air flow chamber 26 near air intake vent 54. Air is drawn into air flow chamber 26 along a path generally indicated by the arrows 76, shown in FIG. 4. Once the drawn air reaches exterior cover 58, the drawn air reverses direction as generally indicated by arrows 78. Once the drawn air passes fan blade 51, such air is exposed to a high pressure plenum within conduit 71 and is expelled from air flow chamber 26 through air exhaust vent 56 in a direction generally indicated by arrows 80.

The apparatus is provided with means for supplying electrical power to motor 50. In the preferred embodiment, such means comprises at least one rechargeable battery 81 operably connected to motor 50 through an electrical power cable 82. As shown in FIG. 3, battery 81 may be secured to upper wall 32. Such placement of battery 81 upon upper wall 32 counter-balances the weight of housing 24 and motor 50 when helmet 22 is lifted to its raised position. Battery 81 may comprise a rechargeable battery that is easily removed from upper wall 32 and/or plugged into a recharging mechanism (not shown).

Light sensitive switch 52, such as a photo-electric, photoconductive, or photo-resistive cell, is appropriately connected to motor 50, battery 81 and power cable 82 to prevent motor 50 from continually operating when not required or necessary. In the preferred embodiment, a bore 84 is made in front wall 28 and light sensitive switch 52 is inserted therein. Light sensitive switch 52 is then secured to front wall 28.

An elongated conduit 86 is provided around the perimeter of light sensitive switch 52. Elongated conduit 86 serves to restrict the immediate area from which the high intensity light is received by light sensitive switch 52. Thus, elongated conduit 86 prevents the inadvertent actuation of motor 50 if a distant welding arc is struck or if sun light or other extraneous light is present.

In addition, light sensitive switch 52 may be positioned upon front wall 28 just above lens 30 so that switch 52 is directed toward the arc during the welding process.

When light sensitive switch 52 is exposed to a high intensity light, such as the light emitted during a welding process, light sensitive switch 52 permits electric power to pass from battery 81 to motor 50. Thus, when exposed to intense light, light sensitive switch 52 actuates the means for drawing and expelling air through air flow chamber 26.

When such high intensity light is extinguished, light sensitive switch 52 causes electrical power to motor 50 to cease, or at least be dramatically reduced, and thereby conserve the electrical energy stored within battery 81.

Figure 1:
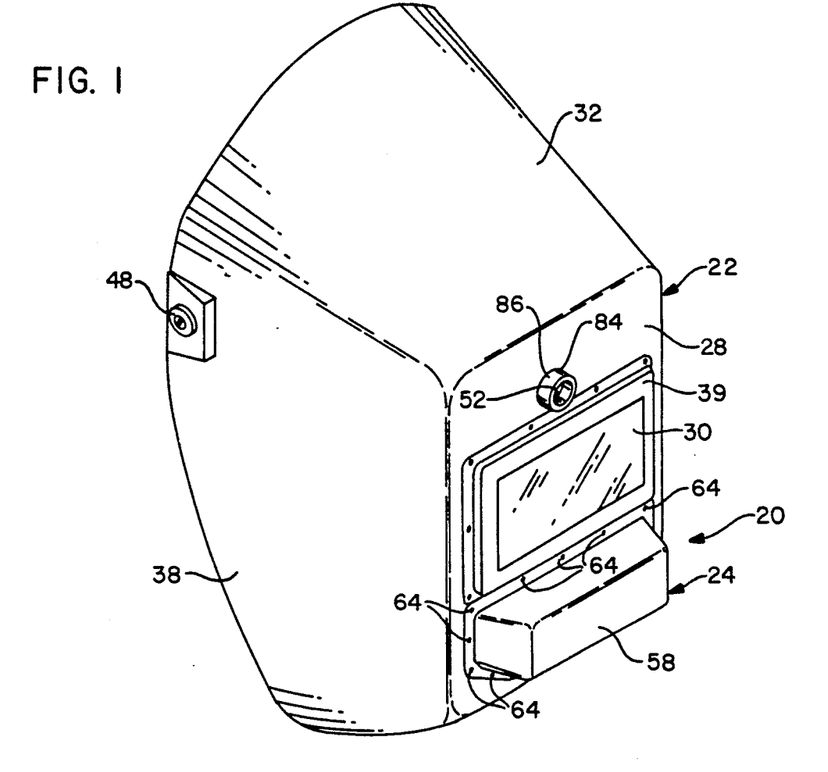
FIG. 1 is an isometric view of the preferred embodiment of the present invention.
Figure 2:
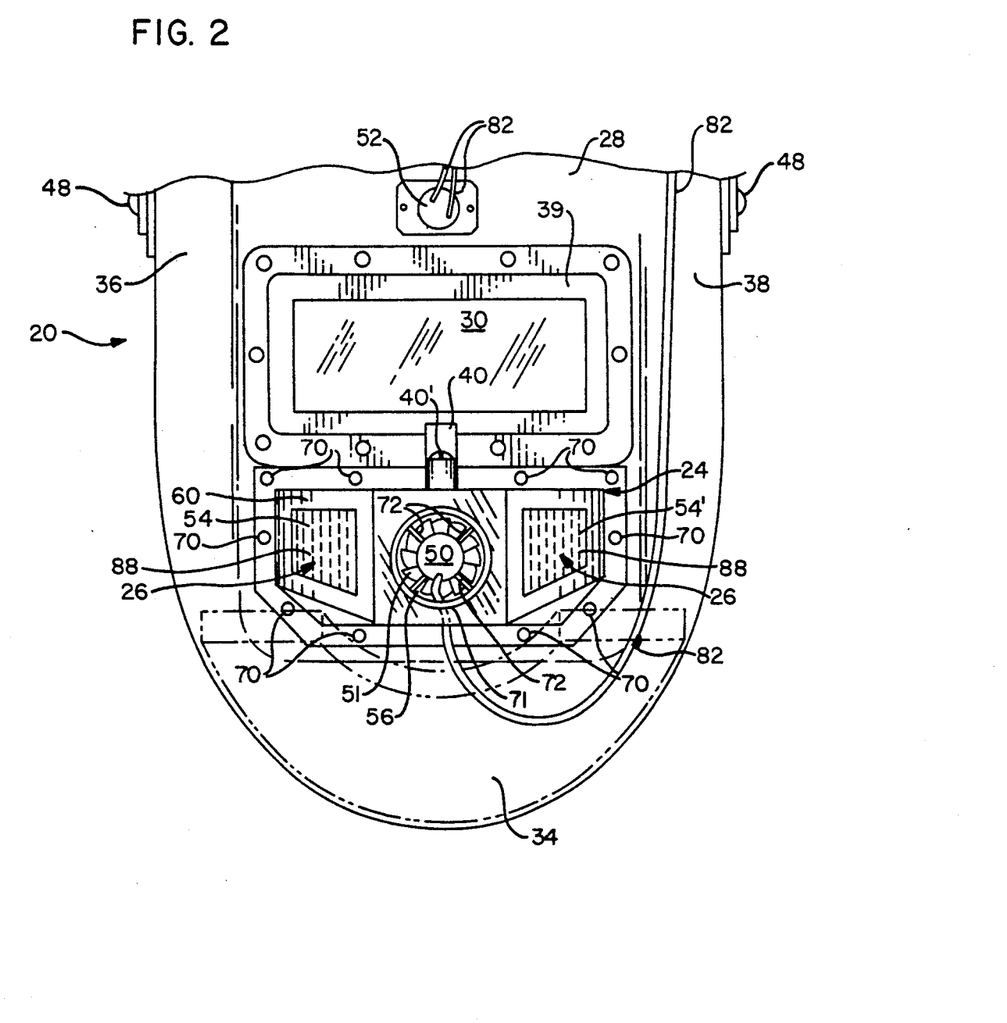
FIG. 2 is a partial, side-elevational view of the apparatus shown in FIG. 1 as seen from the interior side of the hood.

In the preferred embodiment, as shown in FIGS. 2 and 4, system 20 further comprises at least one filter 88 through which contaminated air and vapors are drawn before and/or upon entering air flow chamber 26. This may be accomplished by placing filters 88 at the entrance of air intake vents 54 and 54'. In addition, filters 88 may be retained within a framework 90. Framework 90 may be removably attached to interior element 60 near air intake vents 54 and 54'. Filters 88 may also assume a corrugated configuration to maximize the surface area through which the air may be drawn.

Referring to FIGS. 2-3 and 5-8, welding helmet 22 may also be provided with a smoke block 92 which restricts the entrance of smoke and other contaminated vapors from entering the confines between the interior surface of helmet 22 and the face of person 23. In the preferred embodiment, smoke block 92 is removably secured to lower wall 34 by means of strips of mating hook and loop fasteners 94 and 96 known as Velcro fasteners. Other means of attachment are readily available and may also be used. Alternatively, helmet 22 may incorporate the use of a permanently attached smoke block 92.

Figure 5:
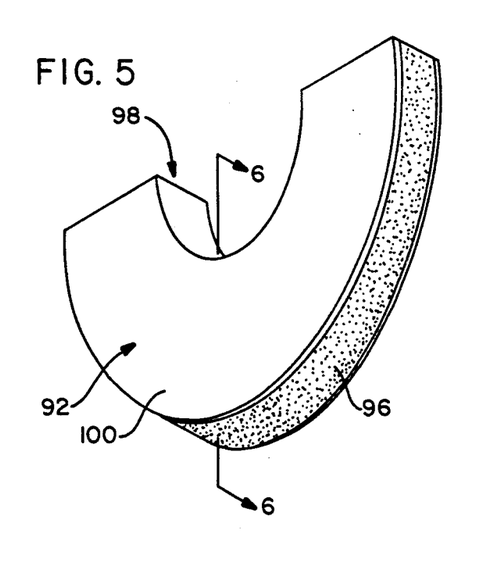
FIG. 5 is an isometric view of the smoke block of the present invention.
Figure 6:
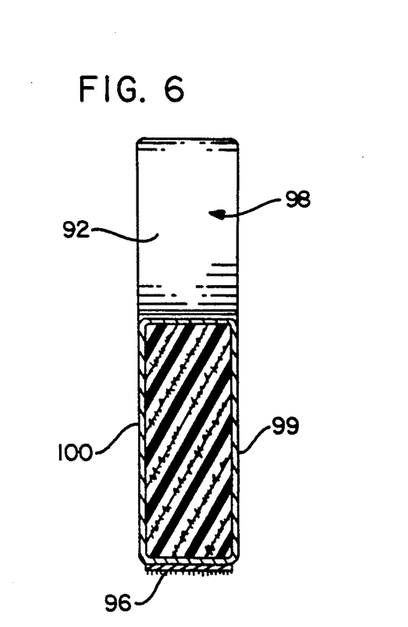
FIG. 6 is a side-elevational view of the smoke block shown in FIG. 5.
Figure 7:
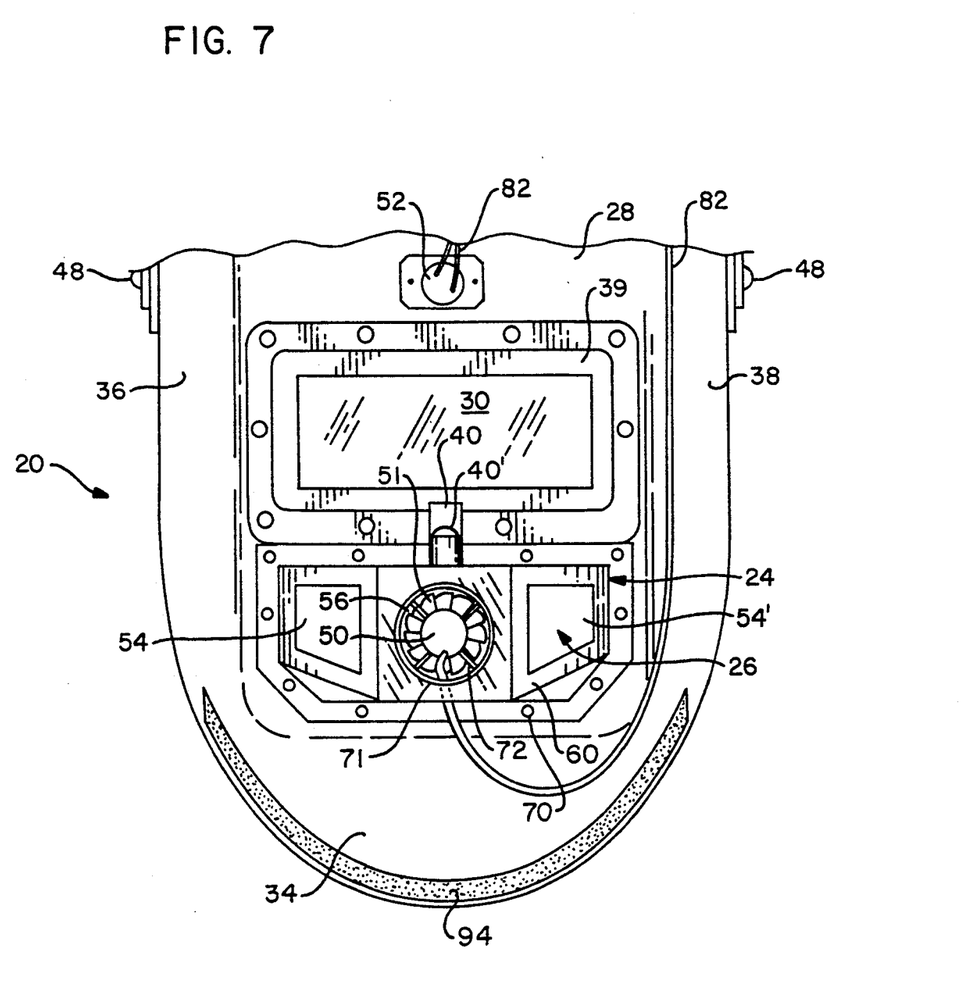
FIG. 7 is a partial, side-elevational view of the apparatus as seen from the interior side of the hood with the smoke block of FIG. 5 removed.
Figure 8:
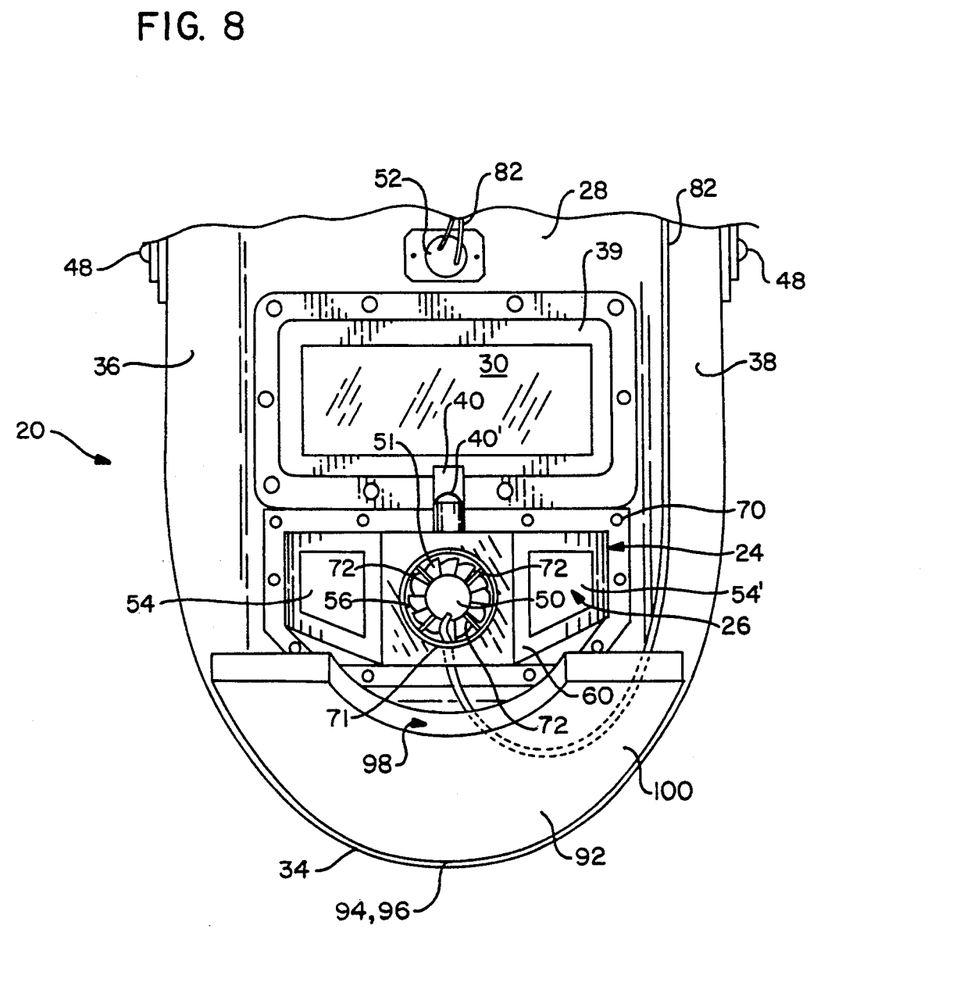
FIG. 8 is a partial, side-elevational view of the apparatus as seen from the interior side of the hood with the smoke block of FIG. 5 in place.

As shown in FIGS. 3, 5 and 8, smoke block 92 is configured to close off the space between lower wall 34 and the neck of person 23. For this reason, smoke block 92 is provided with a form fitted indentation 98 which wraps around the neck of person 23. Smoke block 92 is preferably made of a soft foam rubber 99 covered by soft leather 100 or other durable material.

This invention also discloses and claims a method for circulating and filtering air located between helmet 22 and person 23, comprising the steps of:
(a) automatically drawing air away from an area located between helmet 22 and the facial area of person 23 when a high intensity light is registered by light sensitive switch 52, such high intensity light actuating light sensitive switch 52 thereby causing motor 50 and fan blade 51 to be provided electrical power and therefore rotate, said rotation of fan blade 51 causing air to be drawn away from the facial area of person 23;
(b) passing the drawn air through filter 88; and
(c) expelling filtered air toward the facial area of person 23.

The means and construction disclosed herein are by way of example and comprise primarily the preferred form of putting the invention into effect. Although the drawings depict a preferred and alternative embodiment of the invention, other embodiments have been described within the preceding text. One skilled in the art will appreciate that the disclosed device may have a wide variety of shapes and configurations. Additionally, persons skilled in the art to which the invention pertains might consider the foregoing teachings in making various modifications, other embodiments, and alternative forms of the invention.

It is, therefore, to be understood that the invention is not limited to the particular embodiments or specific features shown herein. To the contrary, the inventor claims the invention in all of its forms, including all alternatives, modifications, equivalents, and alternative embodiments which fall within the legitimate and valid scope of the appended claims, appropriately interpreted under the Doctrine of Equivalents.

INDUSTRIAL APPLICABILITY

The light actuated, air recirculating and filtration system, and methods of use thereof, as described herein may be used to protect the vision and respiration of a welder by providing a conventional welding helmet with automatic means of: breaking up any heavily laden smoke or contaminated vapors which may pass between the helmet and the welder; drawing such air and vapors through a filter; and expelling the filtered air toward the face of the welder. A smoke block may also be used to restrict the entrance of smoke or other contaminated vapors from entering the confines between the helmet and the welder.

The invention offers an apparatus and method for achieving such results without having to continually operate a ventilation fan. Rather, the air recirculating and filtration system of the present invention is only activated when a high intensity light triggers a light sensitive photoconductive cell. Consequently, recirculation and filtration are automatically provided when a welding torch is struck, and is automatically disengaged when the high intensity light is extinguished. A significant amount of electric energy is saved as compared to the electric consumption of continuously run systems. This enables a portable battery pack to be used to power the present system. The need for recharging the batteries is also minimized.

I claim:
1. An apparatus for circulating and/or filtering air between a welding helmet and a wearer, including a welding helmet having a protective front wall, a lens through which a user may view work being performed, and rearwardly extending upper wall, lower wall, left wall, and right wall formed integrally with said front wall, wherein the improvement comprises:
(a) a housing attached to or integrally formed within said helmet, said housing defining an at least partially enclosed air flow chamber having at lest one air intake vent and at least one air exhaust vent;
(b) means for drawing air into said air flow chamber from between said wearer and said helmet through said air intake vent and expelling air located within said air flow chamber outward through said air exhaust vent toward said wearer, said drawing and expelling means having
(i) an electric motor which when actuated rotates at least one fan blade to create a high pressure plenum within said air flow chamber near said air exhaust vent, and
(ii) means of supplying electrical power to said motor;
(c) a light sensitive switch secured to said helmet, said light sensitive switch actuating said drawing and expelling means when said light sensitive switch is exposed to a high intensity light, said light sensitive switch comprising a photoconductive cell, said means of supplying electrical power to said motor having at least one battery operably connected between said electric motor and said light sensitive switch; and

UNITED STATES PATENT AND TRADEMARK OFFICE
CERTIFICATE OF CORRECTION

PATENT NO.  : 5,031,237
DATED       : July 16, 1991
INVENTOR(S) : Gregory S. Honrud It is certified that error appears in the above-identified patent and that said Letters Patent is hereby corrected as shown below:

On column 10, line 46 (which is also Claim 1, line 10), delete "lest" and insert therefor --least--.

On column 10, line 55 (which is also Claim 1, line 19), insert --vacuum plenum within said air flow chamber near said air intake vent, and create a-- between "a" and "high".

Signed and Sealed this

Twelfth Day of January, 1993

Attest:

DOUGLAS B. COMER

*Attesting Officer*     Acting Commissioner of Patents and Trademarks